United States Patent
Teterwak et al.

(10) Patent No.: US 8,188,754 B2
(45) Date of Patent: May 29, 2012

(54) METHOD AND APPARATUS FOR SENSING CAPACITANCE VALUE AND CONVERTING IT INTO DIGITAL FORMAT

(75) Inventors: Jerzy A. Teterwak, Colorado Springs, CO (US); Paul W. Kalthoff, Colorado Springs, CO (US)

(73) Assignee: Maxim Integrated Products, Inc., Sunnyvale, CA (US)

(*) Notice: Subject to any disclaimer, the term of this patent is extended or adjusted under 35 U.S.C. 154(b) by 504 days.

(21) Appl. No.: 12/503,808

(22) Filed: Jul. 15, 2009

(65) Prior Publication Data

US 2011/0012618 A1 Jan. 20, 2011

(51) Int. Cl.
*G01R 27/26* (2006.01)

(52) U.S. Cl. ........................ 324/681; 324/686

(58) Field of Classification Search .............. 324/681, 324/658, 649, 600, 661, 662, 686, 689; 702/47, 702/52
See application file for complete search history.

(56) References Cited

U.S. PATENT DOCUMENTS

| | | | |
|---|---|---|---|
| 3,716,782 A * | 2/1973 | Henry | 324/662 |
| 5,539,323 A * | 7/1996 | Davis, Jr. | 324/690 |
| 6,256,395 B1 | 7/2001 | Melanson | |
| 6,373,264 B1 * | 4/2002 | Matsumoto et al. | 324/667 |
| 6,707,855 B2 | 3/2004 | Patana | |
| 7,391,222 B2 * | 6/2008 | Nishio | 324/662 |
| 2002/0008588 A1 | 1/2002 | Khan | |
| 2004/0090903 A1 * | 5/2004 | Cho et al. | 369/126 |
| 2006/0052074 A1 * | 3/2006 | Minotani et al. | 455/276.1 |

FOREIGN PATENT DOCUMENTS

EP 0782063 A1 2/1997

* cited by examiner

*Primary Examiner* — Hoai-An D Nguyen
(74) *Attorney, Agent, or Firm* — Haverstock & Owens LLP

(57) ABSTRACT

A capacitive sensing system are configured to sense a capacitance value and convert the sensed capacitance value to a digital format. The capacitive sensing system provides good selectivity and immunity to noise and interference, which can be further enhanced by enabling spread spectrum excitation. In some embodiments, the capacitive sensing system utilizes a sinusoidal excitation signal that results in low electromagnetic emissions, limited to narrow frequency band. In some embodiments, the capacitive sensing system is configured to operate in a spread spectrum mode, in which the majority of the excitation signal power is carried in the assigned bandwidth. The excitation frequency and the bandwidth of the spread spectrum excitation signal are programmable in a wide range, which allows for avoiding frequency conflicts in the operating environment.

26 Claims, 8 Drawing Sheets

Phase1 - offset cancellation
Phase2 - full scale measurement
Phase3 - input signal measurement
Phase4 - de-integration phase

METHOD AND APPARATUS FOR SENSING CAPACITANCE VALUE AND CONVERTING IT INTO DIGITAL FORMAT

FIELD OF THE INVENTION

The present invention relates to the field of capacitive sensing. More particularly, the present invention relates to the field of sensing capacitance value and converting the sensed value into digital format.

BACKGROUND OF THE INVENTION

Capacitive sensing is a technology for detecting proximity, position, etc., based on capacitive coupling effects. Capacitive coupling is the transfer of energy within an electrical network by means of the capacitance between circuit nodes. Capacitive coupling is typically achieved by placing a capacitor in series with the signal to be coupled. Capacitive sensing is becoming increasingly popular as a human-device interface technology, for example laptop trackpads and touchscreen displays used in many consumer electronic products, as well as proximity sensing, for example a remote keyless entry system for an automobile, but it is certainly not limited to these applications.

For example, a capacitive touchscreen panel is a sensor typically made of glass coated with a material such as indium tin oxide. This type of sensor is basically a capacitor in which the plates are the overlapping areas between the horizontal and vertical axes in a grid pattern. Since the human body also conducts electricity, a touch on the surface of the sensor will affect the electric field and create a measurable change in the capacitance of the device. These sensors work on proximity, and do not have to be directly touched to be triggered.

In general, there are a number of conventional methods for capacitive sensing. These methods are based on either charge redistribution principle, direct measurement of current through the sensed capacitance, measurement of RC time constant, or measurement of frequency in an oscillator containing the sensed capacitance. Sigma-delta capacitive sensors are a sub-category of the charge redistribution sensors. In many applications, it is important for the capacitive sensor to be immune to interference and noise at frequencies other than the sensor operating frequency. In other words, the capacitive sensor input should exhibit a high level of selectivity and reject all frequencies other than the operating frequency. It is also important that the sensors electromagnetic emission is low and it is band-limited around the operating frequency. The existing capacitive sensors are lacking the above characteristics.

SUMMARY OF THE INVENTION

Embodiments of a capacitive sensing system are configured to sense a capacitance value and convert the sensed capacitance value to a digital format. The capacitive sensing system provides good selectivity and immunity to noise and interference, which can be further enhanced by enabling spread spectrum excitation. In some embodiments, the capacitive sensing system utilizes a sinusoidal excitation signal that results in low electromagnetic emissions, limited to narrow frequency band. In some embodiments, the capacitive sensing system is configured to operate in a spread spectrum mode, in which the majority of the excitation signal power is carried in the assigned bandwidth. Unless otherwise specified, reference herein to an "excitation signal" refers to either a spread spectrum excitation signal or a sinusoidal excitation signal. The excitation frequency and the bandwidth of the spread spectrum excitation signal are programmable in a wide range, which allows for avoiding frequency conflicts in the operating environment. The capacitive system also provides excellent differential linearity of the capacitance-to-digital conversion, immunity to DC current injected into the capacitive sensor input, low complexity, and consumes a low amount of power. The capacitive sensing system can be implemented as part of any device that utilizes proximity or position, including, but not limited to, proximity and touch sensors such as a remote keyless entry system such as used by automobiles, and devices that utilize a touchscreen display, for example a cellular telephone, a personal digital assistant (PDA), a music player such as an MP3 player, and a computing device.

In an aspect, a capacitance sensing device is disclosed. The capacitance sensing device includes a sensed capacitor, a signal generator configured to generate a digital local oscillator signal and an excitation signal, a capacitance-to-amplitude converter coupled to the sensed capacitor and to the signal generator, wherein the capacitance-to-amplitude converter is configured to convert a measured capacitance received from the sensed capacitor to an AC signal according to the excitation signal, the AC signal having an amplitude proportional to the measured capacitance, a demodulator coupled to the capacitance-to-amplitude converter to receive the AC signal and to the signal generator to receive the digital local oscillator signal, wherein the demodulator is configured to output a DC component proportional to the AC signal and to output an AC component, and an analog-to-digital converter coupled to the output of the demodulator, wherein the analog-to-digital converter is configured to output a digital conversion value proportional to the DC component, which is proportional to the measured capacitance. In some embodiments, the signal generator is a direct digital synthesis sine wave generator. The analog-to-digital converter can be configured to completely suppress the AC component output from the demodulator. In some embodiments, the analog-to-digital converter is an integrating analog-to-digital converter having an integration period equal to an integer number of excitation signal cycles, thereby completely suppressing the AC component output from the demodulator. The capacitance sensing device can also include a clock generator coupled to provide a same clock signal to the analog-to-digital converter and to the signal generator. In this case, the signal generator generates the digital local oscillator signal and the excitation signal according to the clock signal. The signal generator can be configured to adjust a phase between the digital local oscillator signal and the excitation signal to compensate for a phase shift in the capacitance-to-amplitude converter. In some embodiments, a phase of the AC signal and the digital local oscillator signal input to the demodulator is in-phase. The capacitance sensing device can also include a digital-to-analog converter coupled between the signal generator and the capacitance-to-amplitude converter. The analog-to-digital converter can be configured to compensate for an offset error and for a sensor gain error of the capacitance sensing device. In some embodiments, the excitation signal is a spread spectrum excitation signal. In other embodiments, the excitation signal is a sinusoidal excitation signal. In some embodiments, the signal generator is configured such that an excitation frequency and a bandwidth of the spread spectrum excitation signal are programmable.

In another aspect, a method of converting a measured capacitance is disclosed. The method includes measuring a capacitance, generating a digital local oscillator signal and a excitation signal, converting the measured capacitance according to the excitation signal to form an AC signal having an amplitude proportional to the measured capacitance, multiplying the AC signal and the digital local oscillator signal to form a demodulated signal with a DC component proportional to the AC signal and an AC component, and converting the demodulated signal to a digital conversion value proportional to the DC component, which is proportional to the measured capacitance. In some embodiments, converting the demodulated signal to the digital conversion completely suppresses the AC component of the demodulated signal. In some embodiments, converting the demodulated signal to a digital conversion includes an integration period that is equal to an integer number of excitation signal cycles, thereby completely suppressing the AC component of the demodulated signal. The method can also include using a same clock signal to generate the digital local oscillator signal and the excitation signal, and to convert the demodulated signal to the digital conversion value. In some embodiments, generating the digital local oscillator signal and the excitation signal includes adjusting a phase between the digital local oscillator signal and the excitation signal to compensate for a phase shift while converting the measured capacitance. In some embodiments, a phase of the AC signal and the digital local oscillator signal is in-phase. The method can also include calibrating an offset error and a sensor gain error before each measurement of the capacitance value. The sensor gain error and the offset error can be compensated by measuring a full-scale capacitance and the offset error prior to each conversion of the measured capacitance. The method can also include compensating for the offset error and for the sensor gain error while converting the capacitance value to the digital conversion value. In some embodiments, the excitation signal is a spread spectrum excitation signal. In some embodiments, an excitation frequency and a bandwidth of the spread spectrum excitation signal are programmable. In some embodiments, a frequency of the spread spectrum excitation signal is continuously swept up and down by varying a frequency control word used to generate the spread spectrum excitation signal. In other embodiments, the excitation signal is a sinusoidal excitation signal.

BRIEF DESCRIPTION OF THE DRAWINGS

Embodiments of the capacitive sensing system are described relative to the several views of the drawings. Where appropriate and only where identical elements are disclosed and shown in more than one drawing, the same reference numeral will be used to represent such identical elements.

DETAILED DESCRIPTION OF THE EMBODIMENTS

Embodiments of the present application are directed to a capacitive sensing system. Those of ordinary skill in the art will realize that the following detailed description of the capacitive sensing system is illustrative only and is not intended to be in any way limiting. Other embodiments of the capacitive sensing system will readily suggest themselves to such skilled persons having the benefit of this disclosure.

Reference will now be made in detail to implementations of the capacitive sensing system as illustrated in the accompanying drawings. The same reference indicators will be used throughout the drawings and the following detailed description to refer to the same or like parts. In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application and business related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

In accordance with the present application, some of the components, process steps, and/or data structures may be implemented using various types of processing systems, including hardware, software, or any combination thereof. In addition, those of ordinary skill in the art will recognize that devices of a less general purpose nature, such as hardwired devices, application specific integrated circuits (ASICs), or the like, may also be used without departing from the scope and spirit of the inventive concepts disclosed herein.

Embodiments of a capacitive sensing system are configured to sense a capacitance value and convert the sensed capacitance value to a digital format. In some embodiments, the capacitive sensing system uses a sinusoidal excitation signal, provides flexibility in selection of the excitation frequency, and operates in spread spectrum mode.

Figure 1:
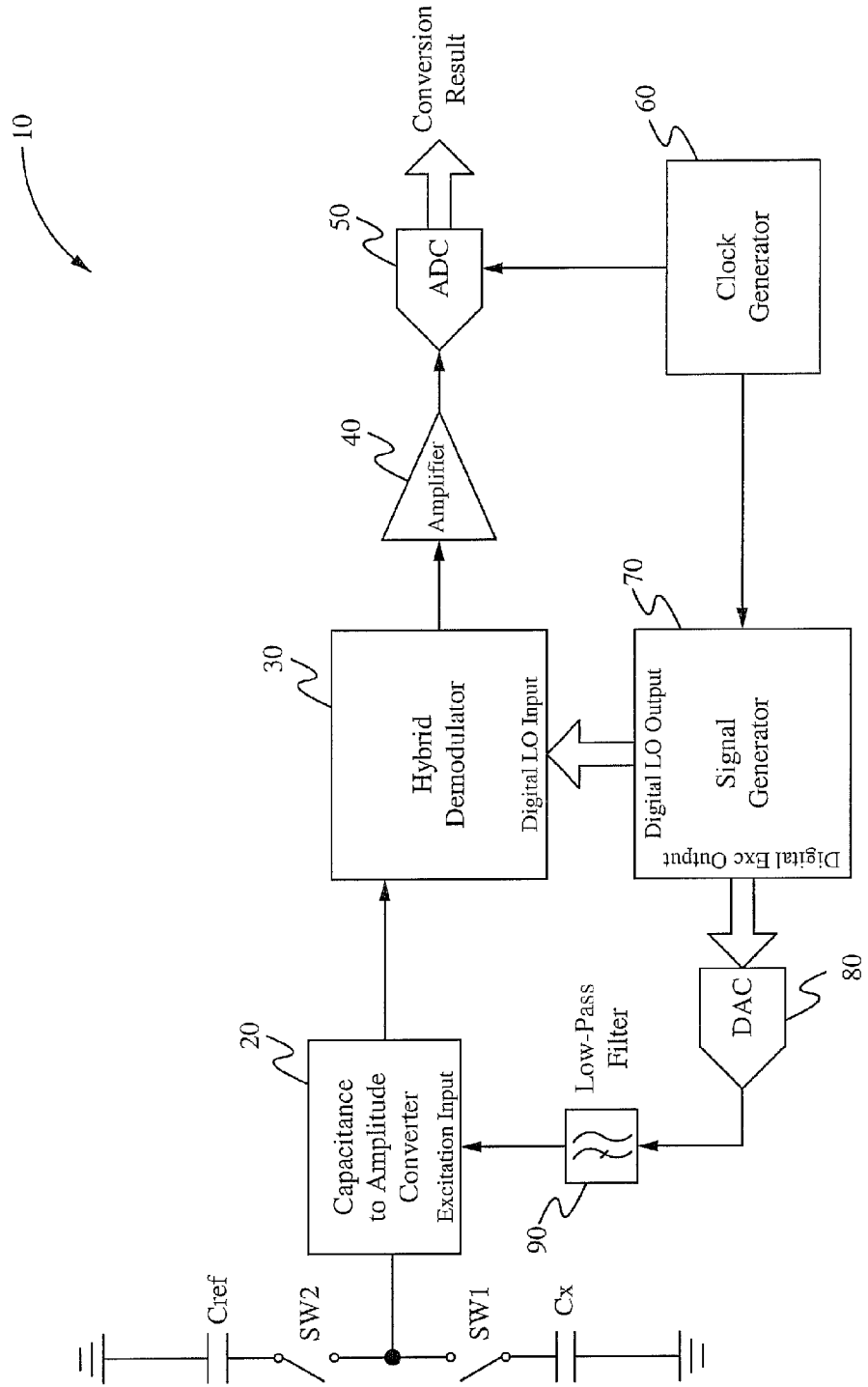
FIG. 1 illustrates an exemplary block diagram of a capacitive sensing system according to an embodiment.

FIG. 1 illustrates an exemplary block diagram of a capacitive sensing system according to an embodiment. A capacitor Cx is a sensed capacitor. During a measurement mode of operation, a switch SW2 is open, and a switch SW1 is closed so that the sensed capacitor Cx is connected to a capacitance-to-amplitude converter 20 and a measured capacitance Cx is input to the capacitance-to-amplitude converter 20. The capacitance-to-amplitude converter 20 also receives as input an excitation signal provided by a signal generator 70. In some embodiments, the signal generator 70 is a direct digital synthesis (DDS) sine wave generator. In some embodiments, the excitation signal is a sinusoidal signal. In other embodiments, the excitation signal is a spread spectrum signal. Within the capacitance-to-amplitude converter 20, the measured capacitance Cx is excited with the sinusoidal or spread spectrum signal. AC current flowing through the measured sensed capacitance is converted to AC voltage in the capacitance-to-amplitude converter 20. The amplitude of the AC signal output from the capacitance-to-amplitude converter 20 is proportional to the measured sensed capacitance. The AC signal is output from the capacitance-to-amplitude converter 20 and input to a hybrid demodulator 30, where the AC signal is demodulated to a DC compliment voltage. The DC voltage output from the hybrid demodulator 30 is proportional to the amplitude of the input AC signal.

The hybrid demodulator 30 also receives as input a digital local oscillator (LO) signal. The AC signal input to the hybrid demodulator 30 is analog, but the input LO signal is digital. Depending on the embodiment, the digital values of the LO signal represent samples of a sinusoidal wave, or a spread spectrum signal. The LO signal is a sequence of binary numbers coded using some number of bits N. In an exemplary implementation, N is equal to four. The values constituting the LO signal are generated in such a way that they are as close as possible to consecutive samples of a sinusoidal wave or a spread spectrum signal. In the hybrid demodulator 30, the analog AC signal is multiplied by the digital LO signal. The two signals are aligned in phase and their multiplication results in a sum of a DC value and an AC signal of frequency being twice the frequency of the multiplied waveforms. The DC value is a DC component proportional to the input AC signal amplitude, and the AC component has a frequency twice the input AC signal frequency.

The signal output from the demodulator 30 is amplified by amplifier 40 and input to an analog-to-digital converter (ADC) 50. In some embodiments, the ADC 50 is a dual slope integrating ADC. In other embodiments, any other conventional ADC can be used. The ADC is clocked by a clock generator 60. The ADC 50 outputs a digital conversion result, which is proportional to the DC component at the output of the hybrid demodulator 30, which in turn is proportional to the sensed capacitance.

The clock generator 60 also provides the clock signal to the DDS sine wave generator 70. In general, DDS is an electronic method for digitally creating arbitrary waveforms and frequencies from a single, fixed source frequency. The DDS sine wave generator 70 digitally generates two output waveforms according to the input clock signal. The first output is connected to a digital-to-analog converter (DAC) 80, which in turn outputs the analog excitation signal input to the capacitance-to-amplitude converter 20 via a low-pass filter 90. The second output is the digital LO signal input to the hybrid demodulator 30. The phase between the two output signals of the DDS sine wave generator 70 is adjusted to compensate for a phase shift in the capacitance-to-amplitude converter 20. The capacitance-to-amplitude converter 20 is an active circuit having some frequency response in the path from the excitation signal input to the converter output. The frequency response describes both amplitude and phase relationship between the input and the output signals. In general, both the signal amplitude and phase will be different at the output than at the input. The phase between the two DDS outputs is adjusted to compensate for the phase shift of the excitation signal in the capacitance-to-amplitude converter 20 and in the low-pass filter 90 at the output of the DAC 80. The phase adjustment is achieved in the digital domain by adding a constant value to a phase accumulator in the DDS sine wave generator 70.

Figure 8:
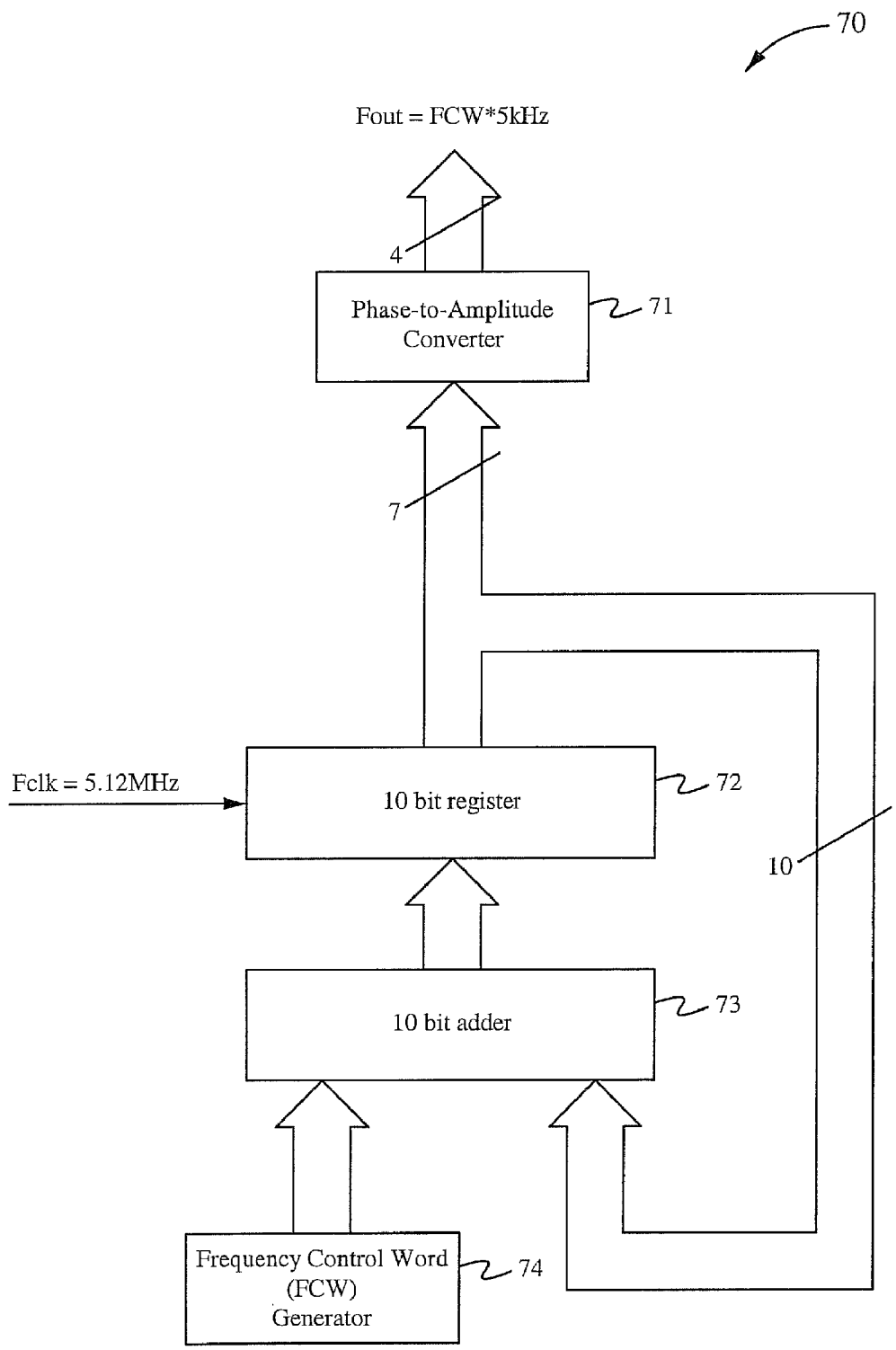
FIG. 8 illustrates an exemplary block diagram of the DDS sine wave generator according to an embodiment.

In some embodiments, the spectral purity requirements for the excitation signal are low, and therefore the complexity of the DDS sine wave generator 70 can also be low. FIG. 8 illustrates an exemplary block diagram of the DDS sine wave generator 70 according to an embodiment. The DDS sine wave generator 70 includes a phase-to-amplitude converter 71, a register 72, an adder 73, and a frequency control word generator 74. The adder 73 functions as a phase accumulator. The phase-to-amplitude converter 71 converts phase generated by the phase accumulator 73 to instantaneous values at the DDS output. In some embodiments, the phase-to-amplitude converter 71 converts linear phase into a sinewave. The input to the DAC 80 (FIG. 1) is connected to the output of the phase-to-amplitude converter 71. In an exemplary implementation, the size of the phase accumulator 73 within the DDS sine wave generator 70 is equal to 10 bits, and the phase is truncated to 7 bits at the input of the phase-to-amplitude converter 71.

Referring again to FIG. 1, the DAC 80 that outputs the excitation signal is a low resolution converter. In an exemplary implementation, a 4-bit DAC is used to synthesize the excitation signal. In some embodiments, the low-pass filter 90 is a reconstruction filter configured to eliminate spectral images generated by the DAC 80. The bandwidth of the low-pass filter 90 is set to accommodate the required frequency range of the excitation signal.

Since the ADC 50 is clocked with the same clock signal as the DDS sine wave generator 70, the integration period equals an integer number of excitation signal cycles. In a dual slope integrating ADC, the integration period is an amount of time, during which, the input signal is integrated in an ADC internal integrator circuit. This results in perfect suppression of the AC components present at the output of the hybrid demodulator 30 without need of other filtering at the output of the hybrid demodulator 30.

The capacitive sensing system 10 includes a sensor gain error and an offset error which need to be compensated for during the conversion of a sensed capacitance. The sensor gain error and offset error are compensated by means of measuring a full scale capacitance and the offset error before each conversion of the sensed capacitance. During an offset cancellation phase, the switches SW1 and SW2 at the input of the capacitance-to-amplitude converter 20 are each opened, thereby disconnecting the full scale reference capacitor Cref and the sensed capacitor Cx. The offset error is then determined with the two capacitors disconnected, as described in relation to FIGS. 4A and 4B below. During a full scale calibration phase, the switch SW1 is open and the switch SW2 is closed, thereby disconnecting the sensed capacitor Cx. The sensor gain error, also referred to as the full-scale error is then determined, as described in relation to FIGS. 4A and 4B below. During a measurement phase, the switch SW1 is closed and the switch SW2 is open, thereby disconnecting the full-scale reference capacitor Cref. The sensed capacitance is then determined as described in detail above, the capacitance measurement result is adjusted to compensate for the determined sensor gain error and the offset error, as described in relation to FIGS. 4A and 4B below.

The capacitive sensing system includes at least the following features. First, the excitation signal is generated in digital domain using a simple DDS circuit. In general, the complexity of a DDS circuit is determined by the length of the phase accumulator, the number of bits driving the phase-to-amplitude converter, the number of bits in the output word, and the requirements for the spectral purity of the output signal. In most applications, a DDS is used to generate a sinusoidal wave of high spectral purity. A conventional "complex" DDS circuit requires the phase accumulator to have width of more than 20 bits, input to the phase-to-amplitude converter being more than 18 bits wide, and the DDS output providing more than 16 bit resolution. The complexity of the phase-to-amplitude converter grows exponentially with the number of input bits. The DDS sine wave generator 70 is "simple" in a sense that it's performance and complexity is substantially lower than in typical DDS implementations. This allows for easy generation of the sinusoidal excitation signal of arbitrary frequency by the DDS sine wave generator 70 without any addition hardware, exact synchronization between the ADC integration cycle time and the excitation signal frequency, and implementation of a hybrid analog/digital demodulator Use of the hybrid analog/digital demodulator is advantageous because of its low complexity, low power consumption, and high accuracy compared to a strictly analog implementation. Additionally, in this system where the LO signal is already synthesized using DDS, the hybrid demodulator integrates a function of a DAC and analog demodulator in one circuit having a complexity lower than the DAC itself. The configuration of the DDS sine wave generator 70 also allows for easy and precise synchronization and phase adjustment of the digital LO signal to the analog AC signal within the hybrid demodulator 30 without need for additional hardware dedicated to for those tasks, and simple implementation of a spread spectrum excitation signal. Spread spectrum limits sensitivity to interference present at some distinct frequency, and also lowers the electromagnetic emissions measured in narrow band around a test frequency.

Second, the capacitive sensing system includes use of the hybrid analog/digital demodulator, which is easy to implement and can be connected directly to the output of the DDS sine wave generator. Third, the ADC 50 is exactly synchronized with the excitation signal frequency, which allows for perfect suppression of AC components present at the demodulator output. Fourth, the offset error and the full scale error are calibrated before each measurement by means of first disconnecting all capacitance from the sensor input and then connecting a known reference capacitance equal to the full scale of the converter. Fifth, the excitation signal is converted from digital to analog in a very simple, low resolution DAC. In this context, "simple" means a lower complexity. For example, in many conventional applications, it is uncommon for a DAC used in signal synthesis to have resolution lower than 8 bits. In an exemplary implementation, a 4-bit DAC 80 is used to synthesize the excitation signal. It is understood that the capacitive sensing system is not limited to theses features, and that other features and related advantages are readily apparent to those skilled in the art.

Figure 2:
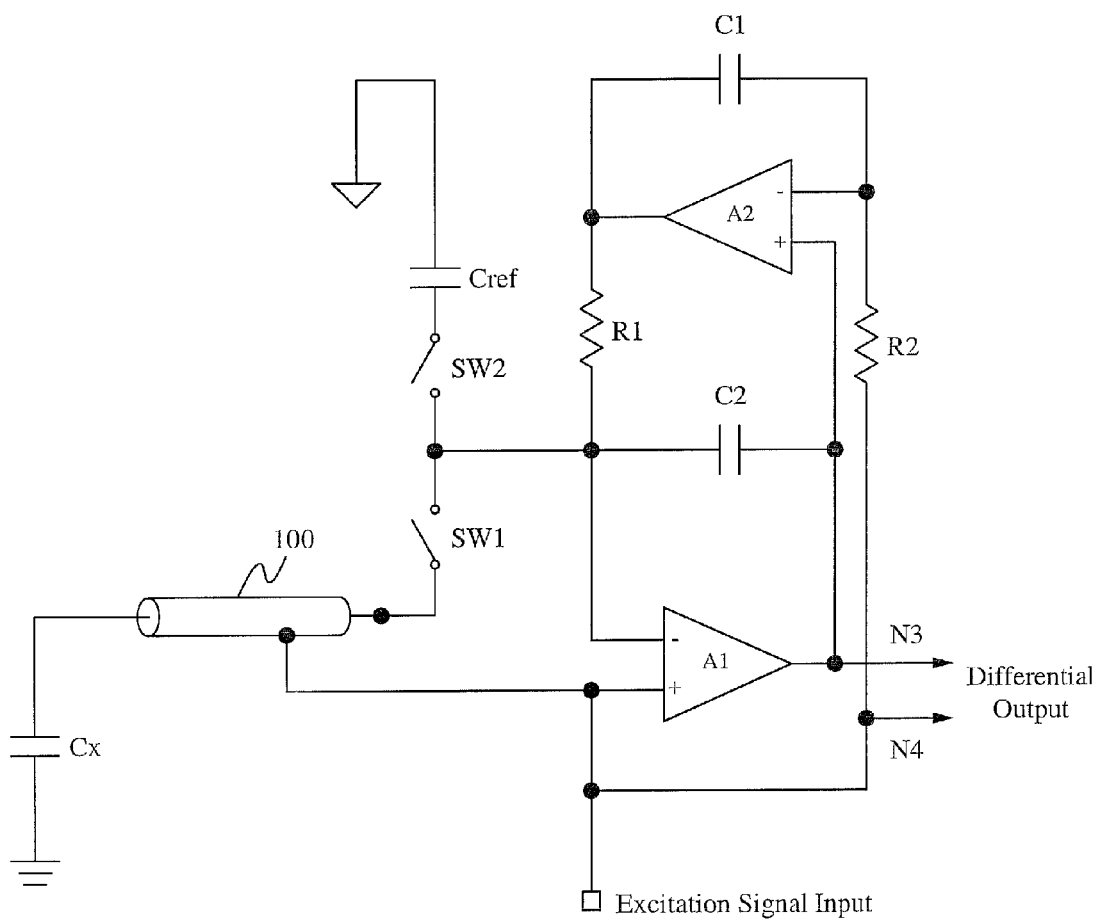
FIG. 2 illustrates an exemplary schematic diagram of the capacitance-to-amplitude converter coupled to the sensed capacitor Cx and reference capacitor Cref of FIG. 1 according to an embodiment.

FIG. 2 illustrates an exemplary schematic diagram of the capacitance-to-amplitude converter 20 coupled to the sensed capacitor Cx and reference capacitor Cref of FIG. 1 according to an embodiment. The capacitance-to-amplitude converter 20 is configured to output an AC signal with an amplitude proportional to the unknown measured capacitance Cx. In FIG. 2, element 100 is added between the capacitor Cx and the switch SW1 to represent the shield of the trace or wire connecting the sensed capacitance to the input of the sensor. In some embodiments, the wire and the shield have the same potential, which effectively cancels the shield capacitance and prevents it from affecting the measurement of the sensed capacitance. The exemplary component elements of the capacitance-to-amplitude converter 20 include an amplifier A1, an amplifier A2, resistors R1 and R2, and capacitors C1 and C2. The output AC signal of the capacitance-to-amplitude converter 20 is represented in FIG. 2 as a differential signal output at the nodes N3 and N4.

The excitation signal received from the output of the low-pass filter 90 is coupled to the non-inverting input of the amplifier A1, and a feedback loop forces the same voltage at the inverting input of the amplifier A1. The feedback loop includes the capacitor C2, the non-inverting input of the amplifier A2, the amplifier A2, the resistor R1, and the inverting input of the amplifier A1. The inverting input of amplifier A1 is connected to the sensed capacitor Cx. The frequency response of the capacitance-to-amplitude converter 20, measured at the differential output, has a character of a high-pass filter response. The operating frequency of the capacitive sensing system 10 is sufficiently high above the corner frequency of the low-pass filter 90, where the frequency response is flat. The corner frequency f0 is calculated from the following formula:

$$f0 = \frac{1}{2\pi\sqrt{R1 \cdot R2 \cdot C1 \cdot C2}}. \quad (1)$$

Above the corner frequency f0, the frequency response is flat, and the output differential signal amplitude is equal to:

$$Vout = Vext\frac{Cx}{C2} \quad (2)$$

where Vext is the excitation voltage amplitude. From the above equation (2) it follows that the output differential signal amplitude is proportional to the measured sensed capacitance Cx. The output differential signal amplitude does not depend on the excitation signal frequency.

The capacitance-to-amplitude converter has a high-pass filter frequency response. As such, the capacitance-to-amplitude converter suppresses any DC current being injected into the sensor input. This prevents any leakage on the printed circuit board from effecting the sensed capacitance measurement. The maximum amount of DC current, which can be suppressed, is determined by the maximum voltage at the output of the amplifier A2 divided by the value of the resistor R1. The topology of the capacitance-to-amplitude converter circuit results in an output amplitude of the AC signal being proportional to the measured sensed capacitance and independent of the excitation frequency.

Figure 3:
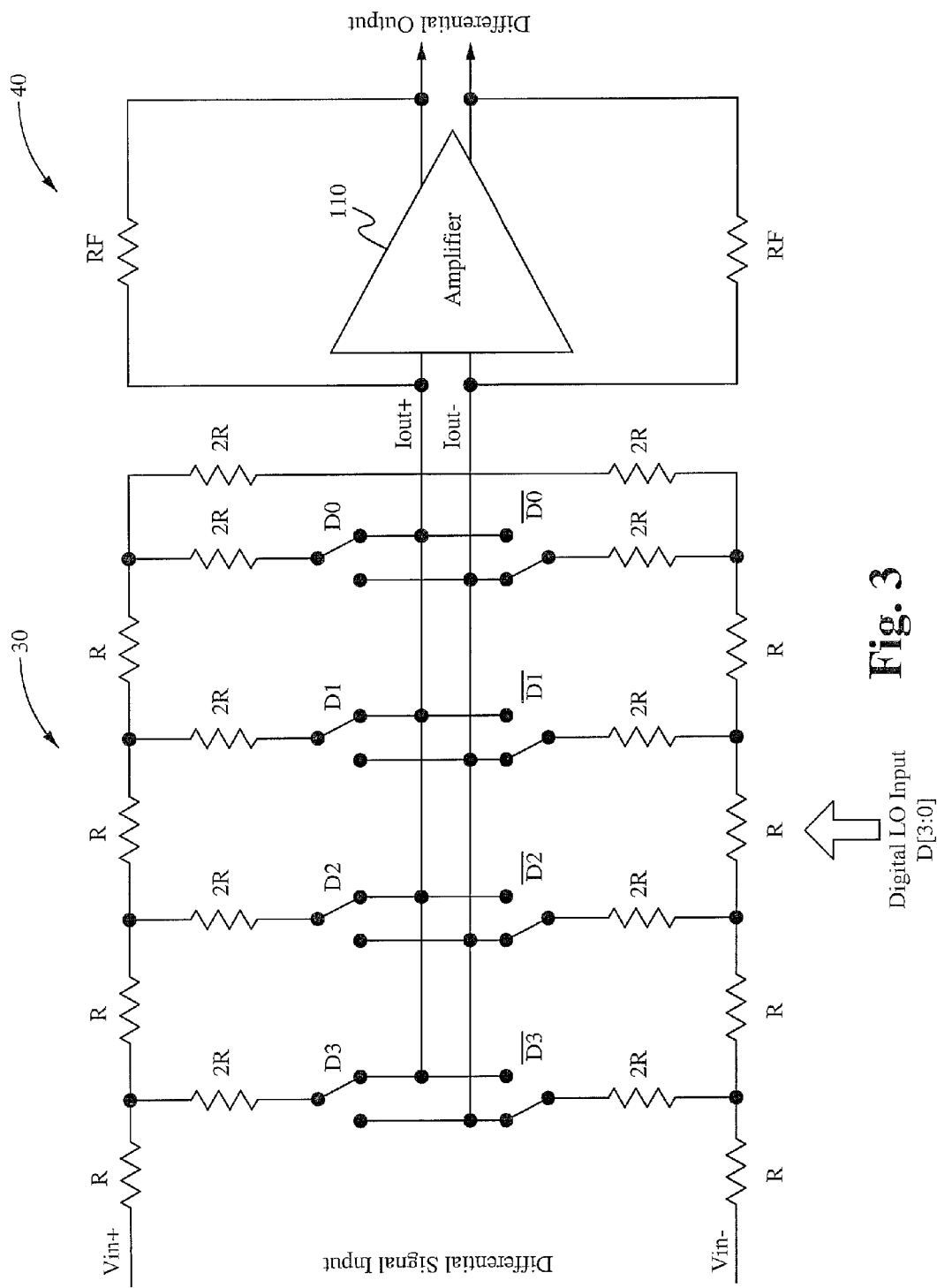
FIG. 3 illustrates an exemplary schematic diagram of the hybrid demodulator and the amplifier of FIG. 1 according to an embodiment.

FIG. 3 illustrates an exemplary schematic diagram of the hybrid demodulator 30 and the amplifier 40 of FIG. 1 according to an embodiment. The exemplary component elements of the hybrid demodulator 30 include multiple resistors R, multiple resistors 2R, and switches D0, D1, D2, D3, $\overline{D0}$, $\overline{D1}$, $\overline{D2}$, $\overline{D3}$. The exemplary component elements of the amplifier 40 include an amplifier 110 and multiple feedback resistors RF. The hybrid demodulator 30 functions similarly to a multiplying R2R DAC. The four bits of the input digital LO signal control the toggle switches D0, D1, D2, and D3. If the corresponding bit has value "1", the toggle switch is connected to the right terminal (as shown in FIG. 3), and if the bit has value "0", the toggle switch is connected to the left terminal. The switches $\overline{D0}$, $\overline{D1}$, $\overline{D2}$, $\overline{D3}$ are controlled by inverted bits of the digital LO signal. The two resistors RF constitute feedback, and through the feedback loop the amplifier 110 forces both inputs Iout+ and Iout− to the same potential. With the same potential at nodes Iout+ and Iout− and no current flowing through the high impedance inputs of the amplifier 110, the current flowing through the two resistors RF can be expressed as:

$$Iout = (((Vin+)-(Vin-))/(4 \cdot R)) \cdot ((2^\wedge-1) \cdot a_3 + (2^\wedge-2) \cdot a_2 + (2^\wedge-3) \cdot a_1 + (2^\wedge-4) \cdot a_0) \quad (3)$$

The coefficients $a_n$ take value 1 if the corresponding bit Dn is "1", or value −1 if the corresponding bit Dn is "0". The current Iout flowing through the resistors RF creates a differential voltage Vout at the output of the amplifier:

$$Vout = 2 \cdot Iout \cdot RF \quad (4)$$

Combining the two equations (3) and (4):

$$V_{out}=(((V_{in+})-(V_{in-}))\cdot(RF)/(2R))\cdot((2^{\hat{}}-1)\cdot a_3+(2^{\hat{}}-2)\cdot a_2+(2^{\hat{}}-3)\cdot a_1+(^{\hat{}}-4)\cdot a_0) \quad (5)$$

Equation (5) shows that the demodulator input differential voltage is multiplied by a value determined by the digital LO input word, as desired.

The hybrid demodulator 30 receives as input the differential signal output from the capacitance-to-amplitude converter 20 of FIG. 2, shown in FIG. 3 as input differential voltage (Vin+)−(Vin−). The hybrid demodulator also receives as input the digital LO signal output from the DDS sine wave generator 70 (FIG. 1). The output of the hybrid demodulator is an output differential current (Iout+)−(Iout−), which is proportional to the input differential voltage and the digital LO signal. The input digital LO signal and the input differential voltage are multiplied together to perform the demodulating function.

The amplifier 110 is configured according to a current-to-voltage converter configuration such that the input differential current (Iout+)−(Iout−) is converted to a voltage. In contrast to a switching demodulator in which a square LO signal switches the sign of an input signal, the hybrid demodulator does not generate sensitivity at odd harmonics of the LO signal frequency. This behavior results in sensor immunity to noise and interference.

Figure 4A:
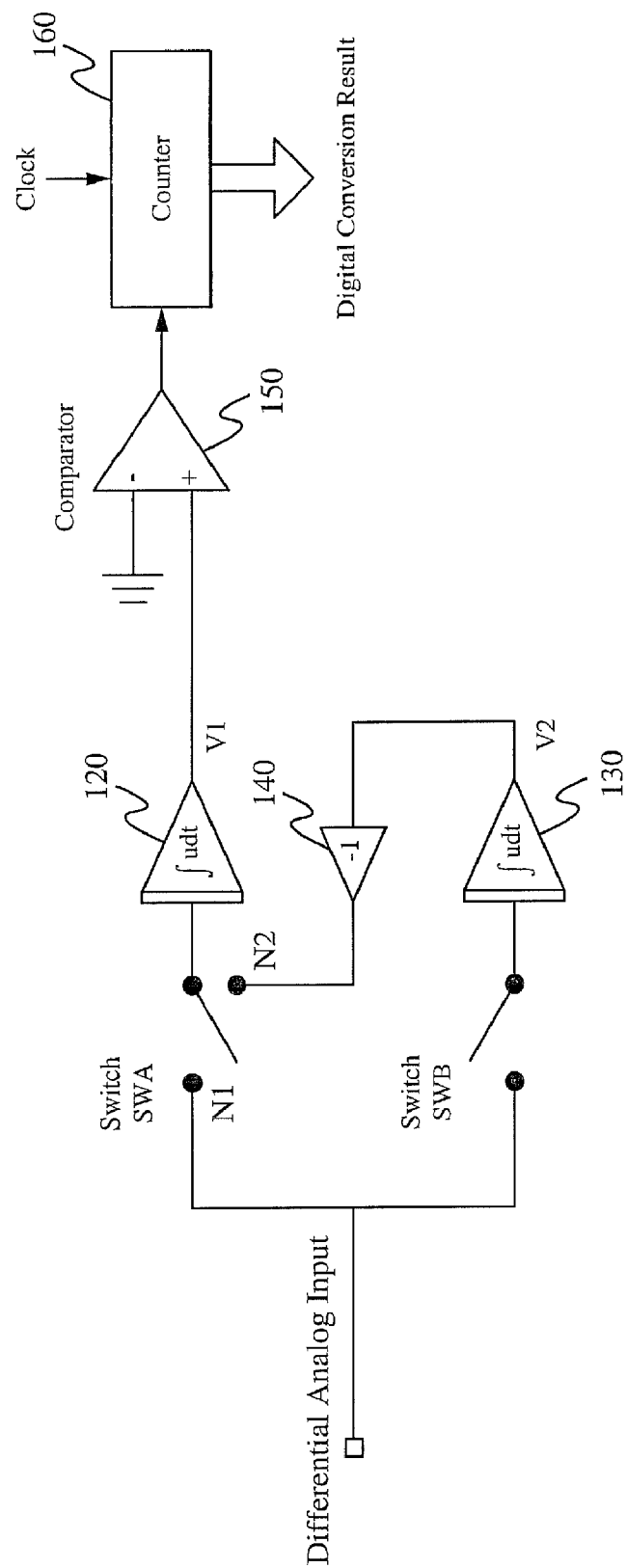
FIG. 4A illustrates an exemplary block diagram of the ADC 50 of FIG. 1 according to an embodiment.

FIG. 4A illustrates an exemplary block diagram of the ADC 50 of FIG. 1 according to an embodiment. The exemplary component elements of the ADC 50 include switches SWA and SWB, an integrator 120, an integrator 130, an inverting buffer 140, a comparator 150, and a counter 160. The ADC 50 is configured to integrate the signal output from the amplifier 40. The signal input to the ADC 50 includes the DC component, proportional to the measured sensed capacitance, and the AC component, which is a byproduct of the synchronous demodulation performed by the hybrid demodulator 30. The integration interval includes an integer number of the AC component cycles, and therefore the integration completely removes the AC component from the ADC input signal. Although shown in FIG. 4A as a single-ended analog input, the input of the ADC is a differential analog signal. However, showing the signal flow in FIG. 4A with a single-ended signal makes the diagram easier to follow, without compromising its accuracy.

Figure 4B:
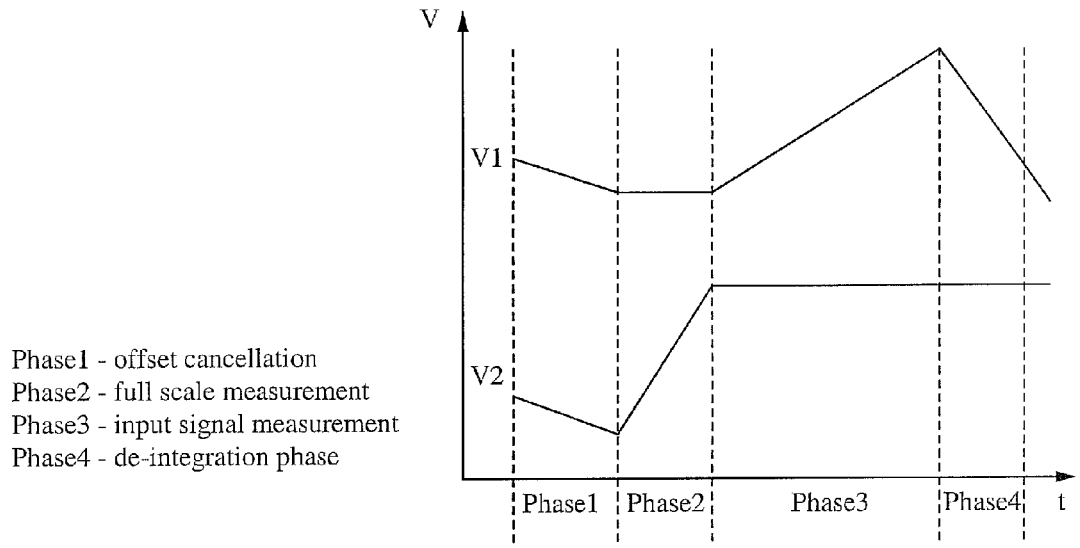
FIG. 4B illustrates an exemplary voltage versus time graph over the four phases for the voltage value V1 at the output of the integrator 120 and the voltage value V2 at the output of the integrator 130 in FIG. 4A.

The conversion performed by the ADC 50 is performed in four phases. FIG. 4B illustrates an exemplary voltage versus time graph over the four phases for the voltage value V1 at the output of the integrator 120 and the voltage value V2 at the output of the integrator 130. In phase one, the input of the sensor is disconnected from all capacitance, that is the capacitance-to-amplitude converter 20 is disconnected from the sensed capacitor Cx and the reference capacitor Cref by opening switches SW1 and SW2 (FIG. 1), and the ADC 50 measures the offset voltage, which is the offset error. The switch SWA is closed on terminal N1 and the switch SWB is closed, thereby coupling the inputs of integrators 120 and 130 to the ADC input, and the offset voltage is integrated in both integrators. During the offset error measurement, the input signal to the ADC 50 is inverted in order to subtract the offset from the ADC conversion result. In the differential configuration, the input signal is inverted by means of swapping the positive and negative inputs to the ADC.

In the second phase, the switch SWA is open, the switch SWB is closed, the switch SW1 (FIG. 1) is open, and the switch SW2 (FIG. 1) is closed. The integrator 120 is disconnected from the ADC input by opening the switch SWA and the integrator 120 holds the voltage integrated in phase one. Switch SW2 (FIG. 1) is closed such that the capacitance-to-amplitude converter 20 is coupled to the reference capacitance Cref. The switch SWB remains closed so that the integrator 130 is coupled to the ADC input, and the integrator 130 integrates the full-scale signal.

In phase three, the switch SWB is open, the switch SWA is closed on the terminal N1, the switch SW1 (FIG. 1) is closed, and the switch SW2 (FIG. 1) is open. The integrator 130 is disconnected from the ADC input by opening the switch SWB, and the integrator 130 holds the full-scale voltage integrated in phase two. The switch SW2 (FIG. 1) is opened and the switch SW1 (FIG. 1) is closed so that the capacitance-to-amplitude converter 20 is coupled to the sensed capacitor Cx. The integrator 120 is coupled to the ADC input through the switch SWA closed on the terminal N1, and the integrator 120 integrates the measured signal.

In phase four, the switch SW1 (FIG. 1) is closed, the switch SW2 (FIG. 1) is open, the switch SWA is closed on terminal N2, and the switch SWB is open. The full-scale voltage stored on the integrator 130 is used as a reference voltage to discharge the integrator 120. The switch SWA closed on the terminal N2 couples the input of the integrator 120 to the output of the integrator 130 through the inverting buffer 140. The length of phase four is used to determine the conversion result. The counter 160 is enabled from the beginning of phase four through the time when the output of the integrator 120 crosses zero volts, at which point the counter is disabled. At the end of phase four, the value in the counter 160 is the A-to-D conversion result, which is the output of the capacitive sensing system 10.

The discharge phase (phase four) duration of the integrator 120 varies with the ADC input signal, and the integrator 120 therefore cannot be used to integrate the reference full scale level. The integrator 130 is used to integrate the full scale reference signal over an integer number of excitation signal cycles. In an exemplary application, the duration of the integration phases are as follows: phase one (offset voltage integration) is 100 usec; phase 2 (reference voltage integration) is 100 usec; phase three (measured signal integration) is 200 usec; phase four (discharge) is up to 100 usec. This resulted in a total conversion time of approximately 500 usec.

The conversion result $C_{ADC}$ output from the counter 160 is expressed by the following equation:

$$C_{ADC} = N_{FS} \frac{T_i}{T_2} \frac{C_x}{C_r} \quad (6)$$

$N_{FS}$ is a full scale code. The full scale code is a digital value at the ADC output, which corresponds to the input capacitance at the high end of the input capacitance range. $T_i$ is an integrator time constant. $T_i$ is the time constant of the integrator 130. $T_2$ is the duration of the reference voltage integration phase, which is the same phase as phase two described above. Cx is the measured sensed capacitance. Cr is the reference capacitance.

The conversion result output from the ADC 50 is independent of the analog front end gain. The DC component at the ADC input (or demodulator output) is proportional to the input capacitance, but the proportionality constant, or gain, is not exactly known and can vary with temperature, power supply voltage, etc. Equation (6) indicates that the proportionality constant does not affect the conversion result, and therefore its variability is irrelevant. The conversion result output from the ADC 50 is also independent of the excitation signal amplitude and the excitation signal frequency. If the full scale error is to be tightly controlled, the full scale error can be trimmed and it will not change due to the excitation frequency or amplitude variation, or changes of the analog front end gain.

In some embodiments, a spread spectrum excitation signal is used to further reduce the circuit sensitivity to electromagnetic interference as well as to reduce the electromagnetic emissions. A spectrum spreading algorithm generates a spread spectrum excitation signal occupying only a specified frequency band and caring little energy outside the band. In the capacitance sensing system 10, due to the way the AC signal components are suppressed in the integrating ADC 50, the spread spectrum excitation signal has to be periodic, with ADC integration time equaling an integer number of the excitation signal periods. These requirements can be met if the spread spectrum excitation signal frequency is continuously swept up and down during the ADC integration phase, which includes the integration phases one, two, and three described above in relation to FIG. 4B. Integration phase four has variable duration, and thus, its duration cannot stay in any fixed relationship to the excitation signal period. The frequency of the spread spectrum excitation signal is swept by means of varying a frequency control word within the DDS sine wave generator 70.

Figure 5:
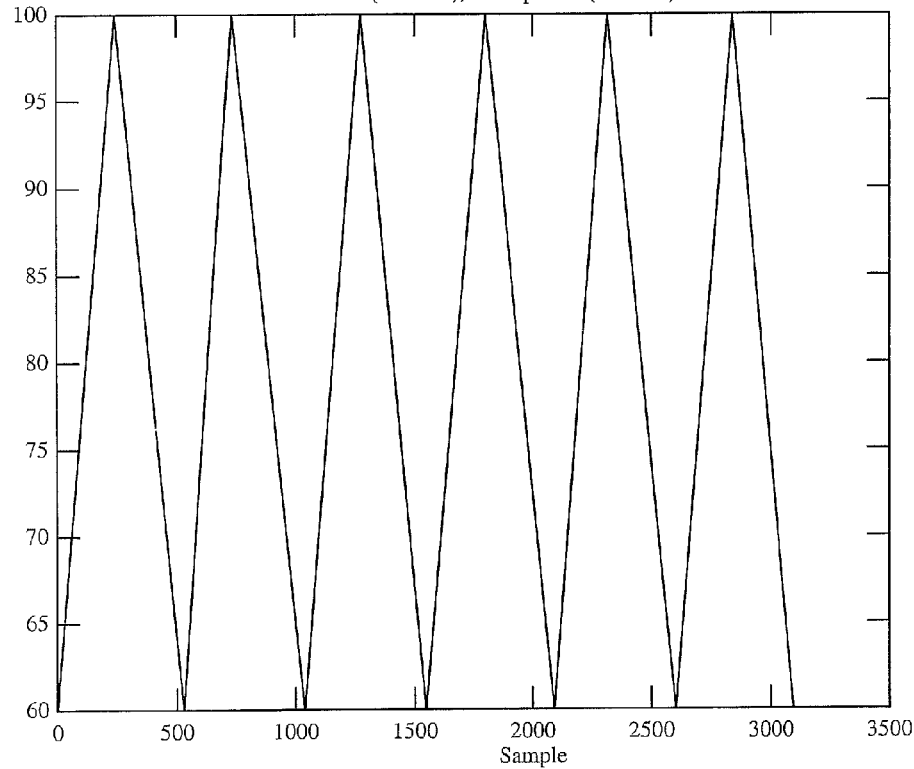
FIG. 5 illustrates a value of an exemplary DDS frequency control word as a function of time in the spread spectrum mode.
Figure 6:
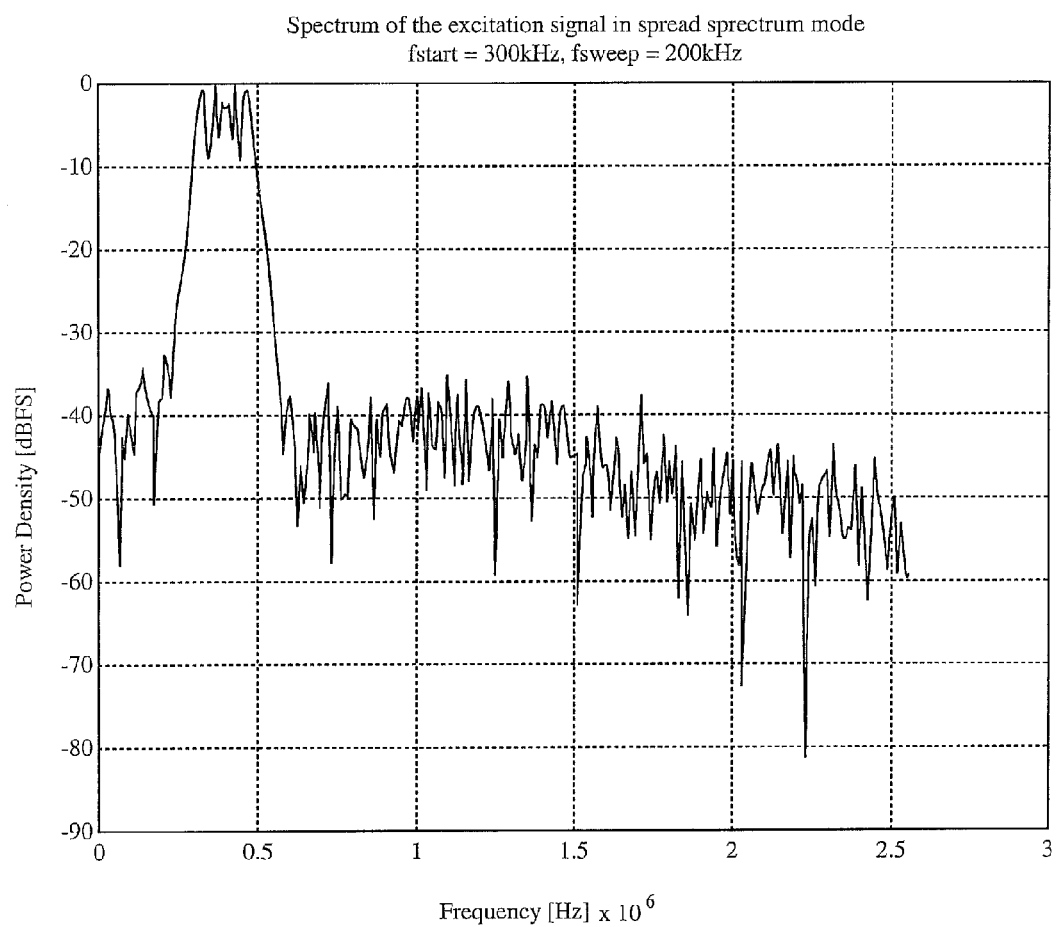
FIG. 6 illustrates an exemplary spectral plot of a spread spectrum excitation signal resulting from application of the DDS frequency control word of FIG. 5.

FIG. 5 illustrates a value of an exemplary DDS frequency control word as a function of time in the spread spectrum mode. The plot of FIG. 5 shows one exemplary implementation, in which the DDS frequency control word is swept with a period of 512 DDS clock cycles, and the DDS phase accumulator length is equal to 10 bits. FIG. 6 illustrates an exemplary spectral plot of a spread spectrum excitation signal resulting from application of the DDS frequency control word of FIG. 5. In order for the spread spectrum excitation signal to be periodic with the same period as the period of the DDS frequency control word sweep, the phase accumulation in the DDS sine wave generator 70 over the frequency control word sweep period has to be a multiple of $2\pi$. Such a condition is met by the frequency control word generator 74 shown in FIG. 7. The frequency control word generator 74 of FIG. 7 is included in the DDS sine wave generator 70 (FIG. 1).

Figure 7:
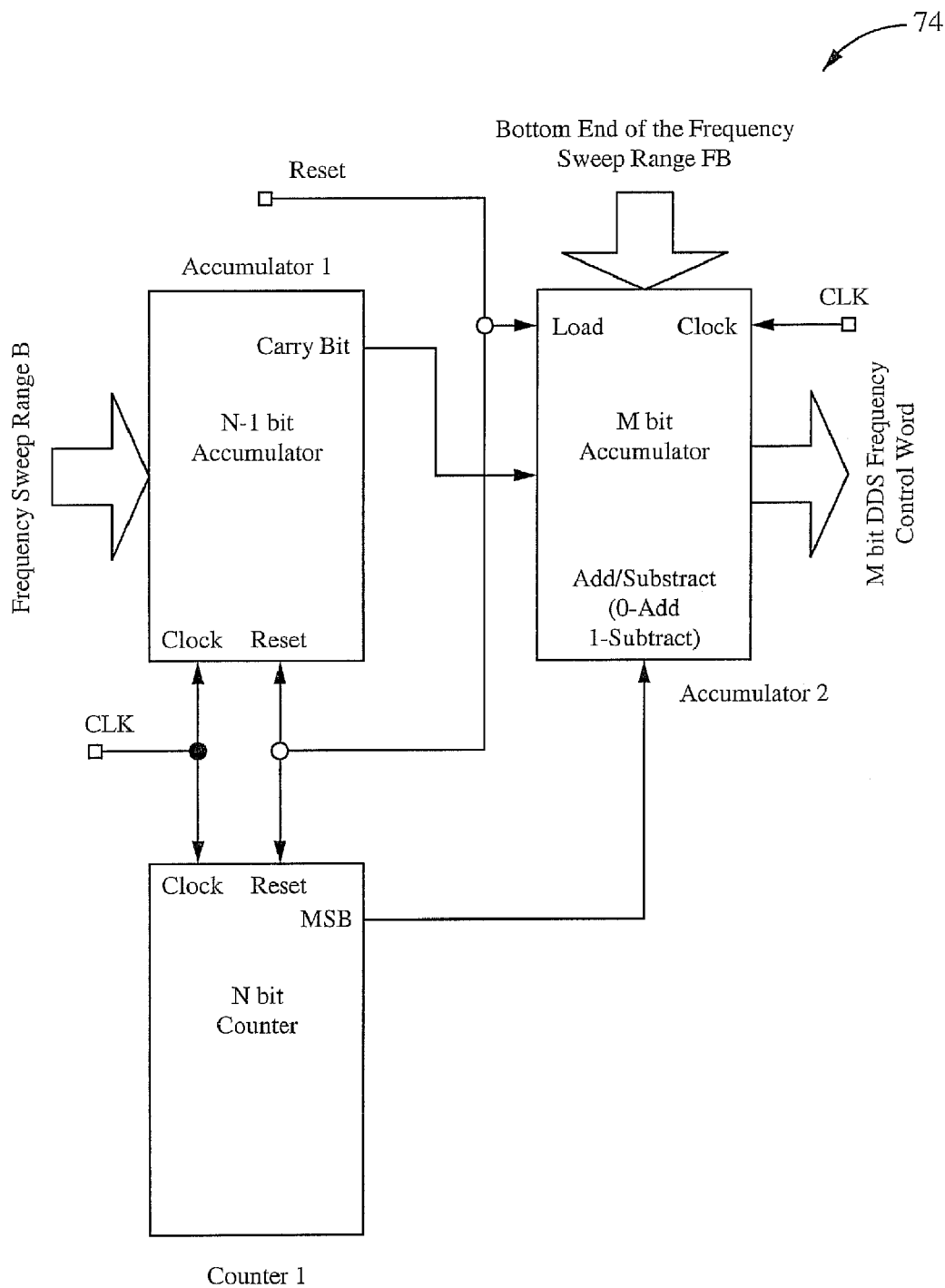
FIG. 7 illustrates an exemplary block diagram of frequency control word generator according to an embodiment.

In the frequency control word generator 74 of FIG. 7, the spread spectrum frequency band is programmed by providing the range of the frequency sweep as input B to the accumulator 1, and writing the bottom end of the frequency range FB, as an initial value in the accumulator 2. If both values B and FB are even, the phase accumulation in the DDS sine wave generator 70 over the frequency control word sweep is a multiple of $2\pi$. If both values B and FB are not even, then the phase accumulation in the DDS sine wave generator 70 over the frequency control word sweep is not a multiple of $2\pi$. The spectrum spreading frequency control word generator generates a strictly periodic signal and allows for easy programmability of the signal frequency range.

If the spread spectrum excitation signal is used, the hybrid demodulator 30 (FIG. 1) becomes a correlator. In general, in a spread spectrum mode, the signal coming to both inputs of the hybrid demodulator 30 (the input from the capacitance-to-amplitude converter 20 and the input from the DDS sine wave generator 70) can be considered random noise. In this case, the multiplication function of the hybrid demodulator 30 results in a DC component, which is proportional to the correlation between the two signals. In this spread spectrum mode, the output signal from the hybrid demodulator 30 still includes the DC component, which is proportional to the input signal amplitude, and the AC component, which is completely suppressed in the integrating ADC 50.

It is understood that the schematic diagrams shown for the capacitance-to-amplitude converter, the hybrid demodulator, the ADC, the DDS sine wave generator, and the frequency control word generator are for exemplary purposes only, and that alternative configurations that result in the same functionality are also contemplated.

The present invention has been described in terms of specific embodiments incorporating details to facilitate the understanding of the principles of construction and operation of the invention. Such references, herein, to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A capacitance sensing device comprising:
   a. a sensed capacitor;
   b. a signal generator configured to generate a digital local oscillator signal and an excitation signal;
   c. a capacitance-to-amplitude converter coupled to the sensed capacitor and to the signal generator, wherein the capacitance-to-amplitude converter is configured to convert a measured capacitance received from the sensed capacitor to an AC signal according to the excitation signal, the AC signal having an amplitude proportional to the measured capacitance;
   d. a demodulator coupled to the capacitance-to-amplitude converter to receive the AC signal and to the signal generator to receive the digital local oscillator signal, wherein the demodulator is configured to output a DC component proportional to the AC signal and to output an AC component; and
   e. an analog-to-digital converter coupled to the output of the demodulator, wherein the analog-to-digital converter is configured to output a digital conversion value proportional to the DC component, which is proportional to the measured capacitance.

2. The capacitance sensing device of claim 1 wherein the excitation signal comprises a spread spectrum excitation signal.

3. The capacitance sensing device of claim 2 wherein the signal generator is configured such that an excitation frequency and a bandwidth of the spread spectrum excitation signal are programmable.

4. The capacitance sensing device of claim 1 wherein the excitation signal comprises a sinusoidal excitation signal.

5. The capacitance sensing device of claim 1 wherein the signal generator comprises a direct digital synthesis sine wave generator.

6. The capacitance sensing device of claim 1 wherein the analog-to-digital converter is configured to completely suppress the AC component output from the demodulator.

7. The capacitance sensing device of claim 6 wherein the analog-to-digital converter comprises an integrating analog-to-digital converter having an integration period equal to an integer number of excitation signal cycles, thereby completely suppressing the AC component output from the demodulator.

8. The capacitance sensing device of claim 1 further comprising a clock generator coupled to provide a same clock signal to the analog-to-digital converter and to the signal generator.

9. The capacitance sensing device of claim 8 wherein the signal generator generates the digital local oscillator signal and the excitation signal according to the clock signal.

10. The capacitance sensing device of claim 1 wherein the signal generator is configured to adjust a phase between the digital local oscillator signal and the excitation signal to compensate for a phase shift in the capacitance-to-amplitude converter.

11. The capacitance sensing device of claim 10 wherein a phase of the AC signal and the digital local oscillator signal input to the demodulator is in-phase.

12. The capacitance sensing device of claim 1 further comprising a digital-to-analog converter coupled between the signal generator and the capacitance-to-amplitude converter.

13. The capacitance sensing device of claim 1 wherein the analog-to-digital converter is configured to compensate for an offset error and for a sensor gain error of the capacitance sensing device.

14. A method of converting a measured capacitance, the method comprising:
 a. measuring a capacitance;
 b. generating a digital local oscillator signal and an excitation signal;
 c. converting the measured capacitance according to the excitation signal to form an AC signal having an amplitude proportional to the measured capacitance;
 d. multiplying the AC signal and the digital local oscillator signal to form a demodulated signal with a DC component proportional to the AC signal and an AC component; and
 e. converting the demodulated signal to a digital conversion value proportional to the DC component, which is proportional to the measured capacitance.

15. The method of claim 14 wherein converting the demodulated signal to the digital conversion completely suppresses the AC component of the demodulated signal.

16. The method of claim 15 wherein converting the demodulated signal to a digital conversion includes an integration period that is equal to an integer number of excitation signal cycles, thereby completely suppressing the AC component of the demodulated signal.

17. The method of claim 14 further comprising using a same clock signal to generate the digital local oscillator signal and the excitation signal, and to convert the demodulated signal to the digital conversion value.

18. The method of claim 14 wherein generating the digital local oscillator signal and the excitation signal includes adjusting a phase between the digital local oscillator signal and the excitation signal to compensate for a phase shift while converting the measured capacitance.

19. The method of claim 18 wherein a phase of the AC signal and the digital local oscillator signal is in-phase.

20. The method of claim 14 further comprising calibrating an offset error and a sensor gain error before each measurement of the capacitance value.

21. The method of claim 20 wherein the sensor gain error and the offset error are compensated by measuring a full-scale capacitance and the offset error prior to each conversion of the measured capacitance.

22. The method of claim 20 further comprising compensating for the offset error and for the sensor gain error while converting the capacitance value to the digital conversion value.

23. The method of claim 14 wherein the excitation signal comprises a spread spectrum excitation signal.

24. The method of claim 14 wherein an excitation frequency and a bandwidth of the spread spectrum excitation signal are programmable.

25. The method of claim 14 wherein a frequency of the spread spectrum excitation signal is continuously swept up and down by varying a frequency control word used to generate the spread spectrum excitation signal.

26. The method of claim 14 wherein the excitation signal comprises a sinusoidal excitation signal.

* * * * *